Figure 1:
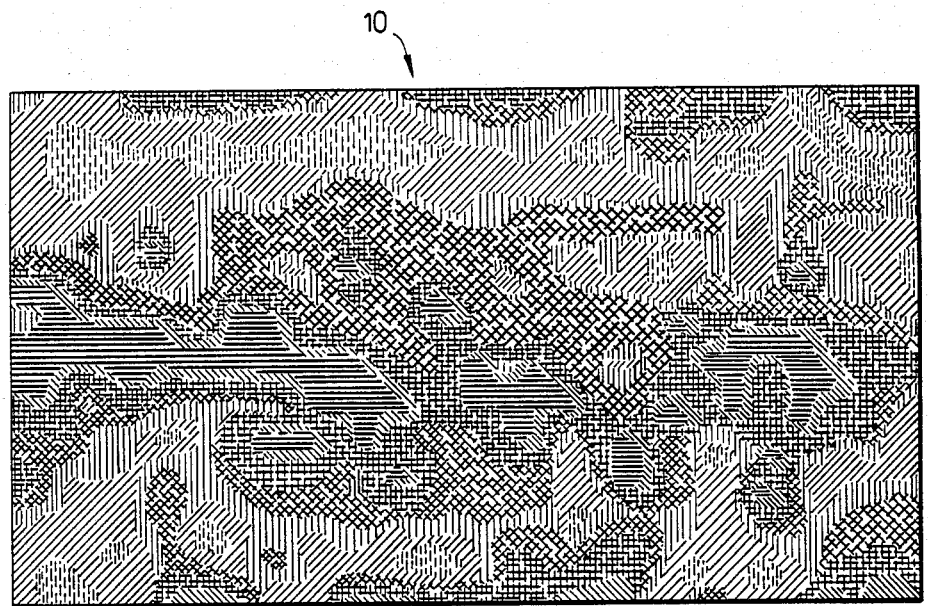

United States Patent [19]

Nicholson et al.

[11] Patent Number: 4,623,434
[45] Date of Patent: Nov. 18, 1986

[54] METHOD OF DETERMINING CATHODIC CORROSION AND DISPLAYING

[76] Inventors: John P. Nicholson, R.R. 5, Orangeville, Canada, L9W 2Z2; Douglas W. Pressley, 71 Celeste Drive, Westhill, Canada, M1E 2E4

[21] Appl. No.: 462,404

[22] Filed: Jan. 31, 1983

[51] Int. Cl.$^4$ ............................................. G01N 27/46
[52] U.S. Cl. ..................................... 204/1 T; 204/404
[58] Field of Search ....................... 204/1 T, 1 C, 404; 374/137, 162; 116/DIG. 41, 206

[56] References Cited

U.S. PATENT DOCUMENTS

| 2,627,682 | 2/1953 | Markey | 116/DIG. 41 |
| 3,153,739 | 10/1964 | Graffenreid | 374/137 |
| 3,493,481 | 2/1970 | Messner et al. | 204/1 T |
| 4,019,129 | 4/1977 | Grau | 204/1 C |
| 4,155,814 | 5/1979 | Tejfallussy et al. | 204/1 C |

OTHER PUBLICATIONS

Gainer et al., *Corrosion*, vol. 35, No. 2, Feb. 1979, pp. 61-67.
Flor et al., *Materials Protection*, Nov. 1965, pp. 49–52.

*Primary Examiner*—T. Tung
*Attorney, Agent, or Firm*—Burgess, Ryan & Wayne

[57] ABSTRACT

The present invention relates to a method of representing corrosion occurring in the reinforced concrete structure and the resultant representation. The representation comprises a display of individual color indicia each representative of electrolytic voltage potential measured at a corresponding location on a surface of the structure. Each color indicia is one of a selected group of distinguishable color indicia and each distinguishable color indicia represents a predetermined range of electrolytic potentials. The method of representing corrosion involves measuring the electrolytic voltage potentials at predetermined locations on the concrete surface, and assigning a displacement co-ordinate to each measurement and a color indicia to each measured value of electrolytic voltage potential. The color indicia is representative of each measured electrolytic voltage potential and is marked on a surface in accordance with the co-ordinates of each measured potential.

3 Claims, 2 Drawing Figures

METHOD OF DETERMINING CATHODIC CORROSION AND DISPLAYING

The present invention relates to a representation of corrosion occurring on a reinforced concrete structure and a method of producing this colour representation. In particular, it relates to a colour representation.

In controlling corrosion within reinforced concrete structures an electrolytic voltage potential survey of the reinforcing steel is commonly made. The purpose of this survey is to determine the extent of corrosion that has occurred and active corrosion occurring in a reinforced concrete structure.

Usually these surveys are conducted by taking measurements at predetermined locations along a relatively flat surface of the reinforced concrete structure. These readings or measurements would commonly be made at a 3 to 5 foot or larger grid distance separation and manually transferred to a graphic representation of the structure. In other words, the value of measured voltage potential would be printed at a point on the graphic representation corresponding to where the measurement for voltage potential was taken.

The problem with such a graphic representation of the corrosion is that the information is difficult to comprehend. A person studying the graphic representation has to make comparisons between relative voltage potential by computing the difference of potential measurements shown. The difficulty in assessing the information is further complicated due to the relatively large structures which may be surveyed such as the various decks of a parking garage. In such instances, several graphic representations may have to be made on large drawing paper to convey all the information.

It is therefore an object of the present invention to provide a more comprehensive representation, and method of producing the representation, of corrosion in a reinforced concrete structure.

In accordance with a broad aspect of the present invention there is provided a representation of corrosion in a reinforced concrete structure. The representation comprises a display of individual colour indicia each representative of electrolytic voltage potential measured at a corresponding location on a surface of said structure. Each colour indicia is one of a selected group of distinguishable colour indicia and each distinguishable colour indicia represents a predetermined range of electrolytic potential.

The term colour indicia used throughout the specification and claims means any colour in the visible spectrum of colours including white and black. These colours may be solid colours or comprise one or more primary colours superimposed on one or more primary colours to give a distinctive colour marking.

The representation provided by the present invention readily indicates to a person observing the representation the location of highly corrosive areas of a concrete structure without having to compare numerical values of voltage potential. Such a representation further permits for the density of measurements displayed on the representation to be considerably greater than the density of numerical representation.

In accordance with another aspect of the present invention there is provided a method of representing corrosion occurring in a reinforced concrete structure. The method comprises the steps of:

(a) measuring electrolytic voltage potentials at predetermined locations on the surface relative to a reference electrode;

(b) assigning to each measurement an x, y and z co-ordinate wherein the x and y co-ordinates relate to the relative position of the measurement and the z co-ordinate relates to the value of measured electrolytic voltage potential;

(c) selecting a plurality of distinguishable colour indicia each one of which represents a predetermined range of electrolytic voltage potentials; and (d) marking the colour indicia representative of each measured electrolytic voltage potential on a receptive surface in accordance with the x and y co-ordinates of each measurement potential.

For a better understanding of the nature and objects of the present invention the preferred embodiment of the present invention will be described with reference to the accompanying diagrammatic drawing which is an example of a representation of corrosion in a steel reinforced concrete structure.

Figure 2:
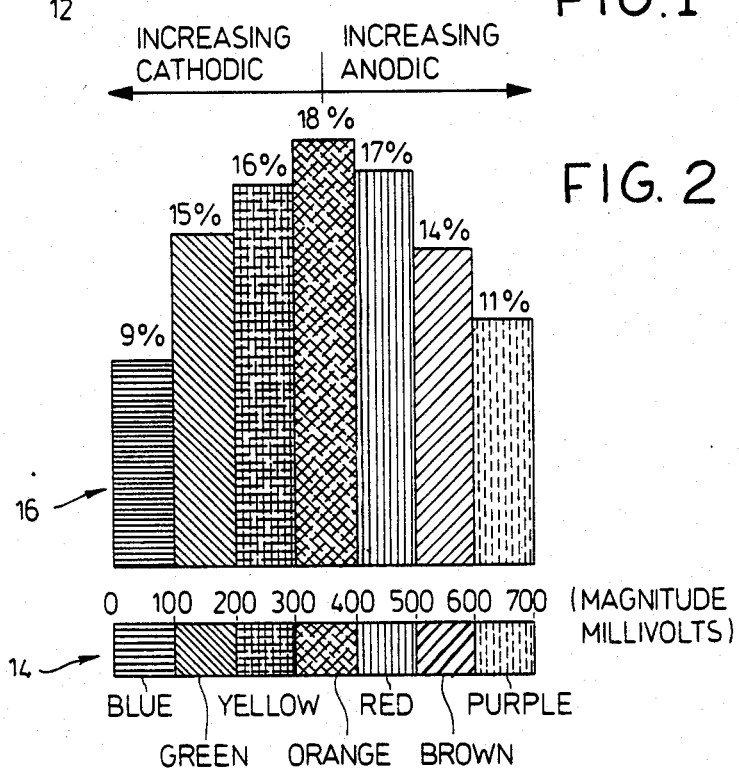

FIG. 1 is colour representation of corrosion in a reinforced concrete structure; and FIG. 2 is a graphical diagram illustrating electrolytic voltages values corresponding to the colour indicia on the representation of FIG. 1.

Referring to the representation 10, the boundary of the reinforced concrete structure is shown by the circumferal rectangular line 12 extending about the outside of the structure. The length and shape of the boundary line corresponds to the length and shape of the concrete structure having potential readings taken from it. Such a structure may be a parking garage deck, a roadway surface, a bridge, silo, tanks or like structure. While only different indicia of black and white colour indicia are shown, it shall be understood that this drawing is an oversimplification of the actual preferred colour representation. It is believed that the number of distinguishable colour indicia in the black, white and gray shades may provide a representation of corrosion but such a representation may not practically show the changes in potential from one area to another in the structure.

The actual preferred representation comprises 39 different distinguishable colour indicia using the three primary colours red, yellow and blue. It should be understood that more or less than 39 colour indicia may be used as long as the extent of corrosion is adequately represented.

Each of the distinguishable colour indicia is chosen to represent a predetermined range of electrolytic voltage potentials. The black and white indicia in the drawing represent distinguishable colours as shown at the bottom of the drawing.

Referring to the representation 10 there are various different colour indicia each plotted at a predetermined location. Some of the colour indicia plotted correspond to an electolytic voltage potential measurement from the structure relative to a reference electrode. The colour indicia representative of measured potentials are plotted on the representation relative to one another and scaled down from the grid pattern used to take the measurements.

The additional or remaining colour indicia plotted on the colour representation are indicative of approximate electrolytic voltage potentials at locations between the measured locations of the structure. These approximated voltage potentials are determined from the measured electrolytic voltage potentials in various directions around each of their locations. This determination is made by looking at the rate of change of electrolytic voltage potential measurements between measured potentials in different directions around the colour indicia to be approximated. This results in what may be referred to as a spline curve for each approximation which curve shows the potential change over a distance. The approximated voltage potential is arrived at by reading the value for voltage potential from the spline curve and assigning to it the corresponding colour indicia.

Below the colour representation of the structure measured there is provided a reference representation of the colour indicia which indicates the range of voltage potentials covered by each of the colour indicia. This representation is shown at 14 and the colour indicia change from the left to right show a continuous increase in the magnitude of electrolytic voltage potential. At approximately halfway across this colour representation 14, the amount of corrosion is such that these portions of the structure displaying the colours should be repaired or replaced. The representation may further provide a tabulated representation 16 which indicates the percentage of the amount of structure having a particular range of voltage potentials. These percentages in tabulated form are shown above each reference representation 14.

While the method of the present invention has been previously described in its broadest aspect, it should be understood that in the preferred method additional steps are incorporated in the method previously described. In the step of marking, further colour indicia are plotted at predetermined locations between the positions corresponding to the measured voltage potentials. These further colour indicia are determined from the rate of change of voltage potentials between measured positions.

The present invention provides a colour representation of corrosion in a steel reinforced concrete structure which representation is more comprehensive than the graphic representations previously provided in the prior art. Further, the colour representation of the present invention is more complex and can convey more information in a given area or size of paper.

In particular it is noted that corrosion in a structure having, for example, length and width dimensions of 480 feet by 480 feet may be scaled down and represented by a colour representation of the present invention having dimensions of 15 inches by 15 inches. When it comes to repair of the structure, measurements can be taken from the representation and scaled to the size of the bridge to determine exactly where repair and replacement of corroded materials should be effected.

The method of the present invention may be readily produced with a computer colour plotter. Each colour indicia may be composed by a pixel of 4 by 4 ink dots of each of the three primary colours. The colour plotter operates in a vertical raster pattern and as such readily lends itself to the serial input of measured values of electrolytic voltage potentials.

With respect to the distance taken between the measurements to provide an adequate representation, it has been found that measurements taken with a 2 foot by 2 foot grid pattern are preferred, however, other grid sizes can be used.

A reference electrode is employed to take the measurements of electrolytic voltage potential.

It should be understood that in instances where noise spikes in the measured readings have a significant influence on the representation, then prior to plotting the colour indicia the computer may calculate an approximate value based on the corresponding measured readings and compare it with the measured reading to determine whether or not the reading falls within a predetermined range about the approximate value. If the measurement falls outside this range, then the plotter would print the approximate value.

The embodiments of the invention in which an exclusive property or privilege is claimed are defined as follows:

1. A method of representing corrosion in a reinforced concrete structure, said method comprising the steps of:
   (a) measuring electrolytic voltage potentials at predetermined locations on said structure;
   (b) deriving at least one further electrolytic voltage potential intermediate said measured voltage potentials and from said measured voltage potentials to indicate the potential gradient between adjacent measured potentials;
   (c) assigning to each measured and derived electrolytic voltage potential an x, y and z coordinate wherein the x and y coordinates relate to the relative position of the respective electrolytic potential voltage on the structure, and the z coordinate relates to the value of the electrolytic voltage potential;
   (d) selecting a plurality of distinguishable colour indicia each one of which represents a predetermined range of electrolytic voltage potentials;
   (e) assigning to each electrolytic voltage potential a colour indicia within whose predetermined range the value of the electrolytic voltage potential lies;
   (f) marking the colour indicia representative of each electrolytic voltage potential on a surface of reduced scale from said structure in accordance with the x and y coordinates of each electrolytic voltage potential to provide a substantially continuous permanent representation of corrosion activity in the structure.

2. A method according to claim 1 wherein said further derived electrolytic voltage potentials are a function of the rate of change of voltage potential between adjacent measured voltage potentials.

3. A method as claimed in claim 1 wherein a plurality of said further electrolytic voltage potentials are derived intermediate said measured potentials.

* * * * *